United States Patent
Aqad et al.

(10) Patent No.: US 9,029,065 B2
(45) Date of Patent: May 12, 2015

(54) PHOTOACID GENERATING COMPOUND AND PHOTORESIST COMPOSITION COMPRISING SAME, COATED ARTICLE COMPRISING THE PHOTORESIST AND METHOD OF MAKING AN ARTICLE

(71) Applicant: Rohm and Haas Electronic Materials LLC, Marlborough, MA (US)

(72) Inventors: Emad Aqad, Northborough, MA (US); Cheng-Bai Xu, Southborough, MA (US); Cong Liu, Shrewsbury, MA (US); Mingqi Li, Shrewsbury, MA (US); Shintaro Yamada, Shrewsbury, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 5 days.

(21) Appl. No.: 13/661,553

(22) Filed: Oct. 26, 2012

(65) Prior Publication Data

US 2014/0120471 A1    May 1, 2014

(51) Int. Cl.
| | | |
|---|---|---|
| G03F 7/004 | (2006.01) | |
| G03F 7/039 | (2006.01) | |
| G03F 7/20 | (2006.01) | |
| G03F 7/32 | (2006.01) | |
| C07C 381/12 | (2006.01) | |
| C07C 309/06 | (2006.01) | |
| C07C 309/04 | (2006.01) | |
| C07C 303/32 | (2006.01) | |
| C07C 309/12 | (2006.01) | |
| C07C 309/17 | (2006.01) | |

(52) U.S. Cl.
CPC ............ *C07C 381/12* (2013.01); *C07C 309/06* (2013.01); *C07C 309/04* (2013.01); *C07C 303/32* (2013.01); *C07C 309/12* (2013.01); *C07C 309/17* (2013.01); *G03F 7/0045* (2013.01); *G03F 7/0046* (2013.01); *G03F 7/0397* (2013.01); *G03F 7/2041* (2013.01); *G03F 7/322* (2013.01); *G03F 7/325* (2013.01)

(58) Field of Classification Search
None
See application file for complete search history.

(56) References Cited

U.S. PATENT DOCUMENTS

| | | |
|---|---|---|
| 5,128,232 A | 7/1992 | Thackeray et al. |
| 7,301,047 B2 | 11/2007 | Yoshida et al. |
| 7,304,175 B2 | 12/2007 | Harada et al. |
| 7,459,260 B2 | 12/2008 | Chandhok et al. |
| 7,488,568 B2 | 2/2009 | Iwai et al. |
| 7,615,330 B2 | 11/2009 | Kamimura et al. |
| 7,718,344 B2 | 5/2010 | Kamimura et al. |
| 7,776,510 B2 | 8/2010 | Iwai et al. |
| 8,227,624 B2 | 7/2012 | Nakayashiki et al. |
| 8,318,403 B2 | 11/2012 | Ichikawa et al. |
| 8,354,217 B2 | 1/2013 | Ichikawa et al. |
| 8,367,298 B2 | 2/2013 | Ichikawa et al. |
| 8,415,082 B2 | 4/2013 | Utsumi et al. |
| 8,420,294 B2 | 4/2013 | Ichikawa et al. |
| 8,507,575 B2 | 8/2013 | Matsumura et al. |
| 2005/0079441 A1 | 4/2005 | Takahashi |
| 2010/0081088 A1 | 4/2010 | Kawaue et al. |
| 2010/0248149 A1 | 9/2010 | Tsuchimura et al. |
| 2010/0316951 A1 | 12/2010 | Ichikawa et al. |
| 2012/0009521 A1 | 1/2012 | Kawaue et al. |
| 2012/0136155 A1 | 5/2012 | Makabe et al. |
| 2013/0344438 A1 | 12/2013 | Aqad et al. |

FOREIGN PATENT DOCUMENTS

| | | |
|---|---|---|
| CN | 102289149 A | 12/2011 |
| JP | 2011201860 A | 10/2011 |
| JP | 2011201866 A | 10/2011 |
| JP | 2011256390 A | 12/2011 |

OTHER PUBLICATIONS

Non-Final Office Action dated Nov. 20, 2014; U.S. Appl. No. 13/925,926; Application filing date Jun. 25, 2013.

*Primary Examiner* — Sin Lee
(74) *Attorney, Agent, or Firm* — Cantor Colburn LLP

(57) ABSTRACT

A compound having the formula (I):

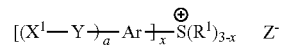

wherein a is an integer of from 1 to 10, and x is an integer of from 1 to 3, $X^1$ comprises a fluoroalcohol, fluorinated ester, or fluorinated anhydride, Y is a single bond, $C_{1-20}$ alkylene group, O, S, NR, ester, carbonate, sulfonate, sulfone, or sulfonamide, wherein R is H or $C_{1-20}$ alkyl, and wherein the $C_{1-20}$ alkylene group is structurally only carbon, or one or more structural carbon atoms in the $C_{1-20}$ alkylene group is replaced by oxygen, carbonyl, ester, or a combination comprising at least one of the foregoing, Ar is a substituted or unsubstituted, $C_5$ or greater monocyclic, polycyclic, or fused polycyclic cycloalkyl; or a substituted or unsubstituted, $C_5$ or greater monocyclic, polycyclic, or fused polycyclic aryl group, wherein the cycloalkyl or aryl is a carbocycle or comprises a heteroatom comprising O, S, N, F, or a combination comprising at least one of the foregoing, each $R^1$ is independently a substituted $C_{5-40}$ aryl, substituted $C_{5-40}$ heteroaryl, $C_{1-40}$ alkyl, a $C_{3-40}$ cycloalkyl, wherein when x is 1, the two groups $R^1$ are separate or bonded to each other to form a $C_{4-40}$ ring structure, and $Z^-$ is a carboxylate, sulfate, sulfonate, sulfamate, or the anion of a sulfonimide, wherein when Y is a single bond, $Z^-$ is not sulfonate.

20 Claims, No Drawings

PHOTOACID GENERATING COMPOUND AND PHOTORESIST COMPOSITION COMPRISING SAME, COATED ARTICLE COMPRISING THE PHOTORESIST AND METHOD OF MAKING AN ARTICLE

BACKGROUND

Advanced lithographic techniques such as 193 nm immersion lithography have been developed to achieve high quality and smaller feature sizes in microlithography processes, for purposes of forming ever-smaller logic and memory transistors. It is important to achieve both smaller critical dimension (CD) in the imaged photoresist used in the microlithography process, and for the photoresists to provide both the lowest line edge roughness (LER) and line width roughness (LWR), while still retaining good process control tolerances such as high exposure latitude (EL) and a wide depth of focus (DOF).

To meet the challenges for resist materials raised by high resolution lithography, photoacid generators (PAGs) have been made which are soluble in aqueous developers and have low absorbance. A variety of photoacid generators (PAGs) used for formulating photoresists are found in prior art, such as those having fluorine-containing cations as disclosed in U.S. Patent Application Publication No. 2005/0079441 A1. However, a need remains for photoresist compositions including PAGs having controlled solubility characteristics in both aqueous and non-aqueous solvents, as well as diffusion control and attendant properties such as resist profile.

STATEMENT OF INVENTION

One or more of the above and other deficiencies of the prior art may be overcome by a photoacid generator compound in accordance with the invention, having the formula (I):

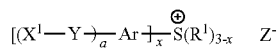

wherein a is an integer of from 1 to 10, and x is an integer of from 1 to 3, $X^1$ comprises a fluoroalcohol, fluorinated ester, or fluorinated anhydride, Y is a single bond, $C_{1-20}$ alkylene group, O, S, NR, ester, carbonate, sulfonate, sulfone, or sulfonamide, wherein R is H or $C_{1-20}$ alkyl, and wherein the $C_{1-20}$ alkylene group is structurally only carbon, or one or more structural carbon atoms in the $C_{1-20}$ alkylene group is replaced by oxygen, carbonyl, ester, or a combination comprising at least one of the foregoing, Ar is a substituted or unsubstituted, $C_5$ or greater monocyclic, polycyclic, or fused polycyclic cycloalkyl; or a substituted or unsubstituted, $C_5$ or greater monocyclic, polycyclic, or fused polycyclic aryl group, wherein the cycloalkyl or aryl is a carbocycle or comprises a heteroatom comprising O, S, N, F, or a combination comprising at least one of the foregoing, each $R^1$ is independently a substituted $C_{5-40}$ aryl, substituted $C_{5-40}$ heteroaryl, $C_{1-40}$ alkyl, a $C_{3-40}$ cycloalkyl, wherein when x is 1, the two groups $R^1$ are separate or bonded to each other to form a $C_{4-40}$ ring structure, and $Z^-$ is a carboxylate, sulfate, sulfonate, sulfamate, or the anion of a sulfonimide, wherein when Y is a single bond, $Z^-$ is not sulfonate.

A photoresist, comprises the photoresist compound and a polymer having acid labile protecting groups.

A coated substrate, comprising: (a) a substrate having one or more layers to be patterned on a surface thereof; and (b) a layer of a photoresist composition of claim 8 over the one or more layers to be patterned.

A method of making a relief image, comprising coating a substrate with a photoresist layer comprising a polymer having acid deprotectable groups, and a compound having the formula (I):

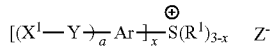

wherein a is an integer of from 1 to 10, and x is an integer of from 1 to 3, $X^1$ comprises a fluoroalcohol, fluorinated ester, or fluorinated anhydride, Y is a single bond, $C_{1-20}$ alkylene group, O, S, NR, ester, carbonate, sulfonate, sulfone, or sulfonamide, wherein R is H or $C_{1-10}$ alkyl, and wherein the $C_{1-20}$ alkylene group is structurally only carbon, or one or more structural carbon atoms in the $C_{1-20}$ alkylene group is replaced by oxygen, carbonyl, ester, or a combination comprising at least one of the foregoing, Ar is a substituted or unsubstituted, $C_5$ or greater monocyclic, polycyclic, or fused polycyclic cycloalkyl; or a substituted or unsubstituted, $C_5$ or greater monocyclic, polycyclic, or fused polycyclic aryl group, wherein the cycloalkyl or aryl is a carbocycle or comprises a heteroatom comprising O, S, N, F, or a combination comprising at least one of the foregoing, each $R^1$ is independently a substituted $C_{5-40}$ aryl, substituted $C_{5-40}$ heteroaryl, $C_{1-40}$ alkyl, a $C_{3-40}$ cycloalkyl, wherein when x is 1, the two groups $R^1$ are separate or bonded to each other to form a $C_{4-40}$ ring structure, and $Z^-$ is a carboxylate, sulfate, sulfonate, or the anion of a sulfonimide, wherein when Y is a single bond, $Z^-$ is not sulfonate; patternwise exposing the photoresist composition layer to actinic radiation; and developing the pattern by treatment with an aqueous alkaline developer to form a positive tone relief image, or with an organic solvent developer to form a negative tone relief image.

DETAILED DESCRIPTION

Disclosed herein are novel substituted onium cations and corresponding photoacid generator (PAGs) composed of the cation and an appropriate anionic moiety. The cationic portion of the photoacid generator includes a sulfonium cation with at least one aromatic group, and at least one fluorinated group such as a fluoroalcohol or the ester of a fluoroalcohol, spatially segregated from and connected to the aromatic group through a heteroatom-containing connecting group (e.g., an alkylene, ether, ester, carbonate, sulfonate, sulfone, sulfonimide, etc.). The fluorinated group further possesses a base-reactive proton, preferably with a pKa of less than or equal to 12, and is reactive with, for example, positive tone (alkaline) developers including metal ion free developers.

The PAGs have high solubility of at least 5 wt % in both alkaline developer and organic solvents. Such solubility properties allow for the use of these PAGs with a variety of organic developers used for Negative Tone-Development (NTD) photoresist processing, as well as in Positive Tone-Development (PTD) basic developers. Furthermore, the high solubility of the PAGs in organic solvents typically used for photoresist formulation, edge bead removal, etc. provides for uniform PAG distribution in the photoresist film. Uniform PAG distribution throughout a photoresist film can provide enhanced photoresist resolution, reduced line edge roughness (LER) and linewidth roughness (LWR) and improved pattern profile relative to PAGs which do not possess the spatially segregated fluorinated groups with base-reactive protons. Such PAGs solubility in NTD and PTD developers can provide patterned photoresists having a low defectivity (LER and LWR).

As used herein, "substituted" means including a substituent such as a halogen (i.e., F, Cl, Br, I), hydroxy, amino, thiol, carboxyl, carboxylate, amide, nitrile, thiol, sulfide, disulfide, nitro, a $C_{1-10}$ alkyl, a $C_{1-10}$ alkoxy, a $C_{6-10}$ aryl, a $C_{6-10}$ aryloxy, a $C_{7-10}$ alkyl aryl, a $C_{7-10}$ alkyl aryloxy, or a combination comprising at least one of the foregoing. As used herein, "alkyl aryl" refers to any combination of an alkyl group and aryl group with any order of structural connectivity. Similarly, "alkyl aryloxy" refers to any combination of an alkyl group and aryloxy group with any order of structural connectivity. It will be understood that any group or structure disclosed with respect to the formulas herein may be so substituted unless otherwise specified, or where such substitution would significantly adversely affect the desired properties of the resulting structure. Also as used herein, the prefix "halo-" means that the group includes any halogen or combination thereof (F, Cl, Br, I). A preferred halogen is fluorine.

Thus, a photoacid generator comprises a compound having the formula (I):

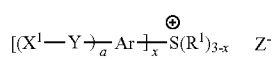

wherein a is an integer of from 1 to 10, preferably from 1 to 6, and also preferably 1 to 4; and x is an integer of from 1 to 3, preferably 1.

In formula (I), $X^1$ is a fluorinated group comprising a base-reactive proton. Preferably, $X^1$ comprises a fluoroalcohol; fluorinated ester or fluorinated anhydride. "Fluoro-" unless otherwise specified includes any group comprising one or more fluorine atom substituents. Exemplary such fluorinated groups include fluoroalcohol groups such as 1,1,1,3,3,3-hexafluoroisopropanol-2-yl, trifluoromethanol, 2,2,2-trifluoroethanol, perfluoroethanol, and perfluorobutanol. Likewise, fluorinated ester groups or fluorinated anhydride groups are ester or anhydride groups containing fluorine at any substitution point on the group. Preferably, a fluoroester group is the mono or diester of a fluoroalcohol. Also as used herein, the prefix "semifluoro-" means wherein a fluorinated group includes more than one fluorine group, but where fewer than 90% of the available protons are fluorinated. Further, the prefix "perfluoro-" as used herein means wherein greater than 90%, preferably greater than 95%, and more preferably greater than 99% of protons in the parent compound are replaced by fluorine atoms. Preferably, $X^1$ is a 1,1,1,3,3,3-hexafluoroisopropanol-containing group or the ester of a $C_{1-20}$ semifluoro- or perfluoroalcohol.

In formula (I), Y is a $C_{1-20}$ alkylene group, O, S, NR, ester, carbonate, sulfonate, sulfone, or sulfonamide, wherein R is H or $C_{1-20}$ alkyl, and wherein the $C_{1-20}$ alkylene group is structurally only carbon, or one or more structural carbon atoms in the $C_{1-20}$ alkylene group is replaced by oxygen, carbonyl, ester, or a combination comprising at least one of the foregoing. Preferably, Y is —O—, —S—, NR—, —O—C(C=O)—, —C(=O)—O—, —O—C(C=O)—O—, —OCH$_2$—(C=O)O—, —OCH$_2$C(=O)—, —SO$_2$—, —O—SO$_2$—, or a combination comprising at least one of the fore going groups, wherein R is H or $C_{1-6}$ alkyl.

Also in formula (I), Ar is a substituted or unsubstituted, $C_5$ or greater monocyclic, polycyclic, or fused polycyclic cycloalkyl; or a substituted or unsubstituted, $C_5$ or greater monocyclic, polycyclic, or fused polycyclic aryl group, wherein the cycloalkyl or aryl is a carbocycle or comprises a heteroatom comprising O, S, N, F, or a combination comprising at least one of the foregoing. Preferably, Ar is a monocyclic, polycyclic, or fused polycyclic $C_{5-40}$ aromatic group, optionally comprising a heteroatom comprising O, S, N, F, or a combination comprising at least one of the foregoing. Also preferably, Ar is a substituted or unsubstituted phenylene, naphthylene, anthracenylene, phenanthrenylene, quinolinylene, dibenzothiophenylene, thioxanthone, thiooxaanthracenylene, or a combination comprising at least one of the foregoing.

Each $R^1$ in formula (I) is independently a substituted $C_{5-40}$ aryl, substituted $C_{5-40}$ heteroaryl, $C_{1-40}$ alkyl, a $C_{3-40}$ cycloalkyl, wherein when x is 1, the two groups $R^1$ are separate or bonded to each other to form a $C_{4-40}$ ring structure. Preferably, each $R^1$ is independently a substituted $C_{5-20}$ aryl or a $C_{1-20}$ alkyl, wherein when x is 1, the two groups $R^1$ are separate or bonded to each other to form a $C_{4-20}$ ring structure.

In formula (I), $Z^-$ is the anion of an acid is a carboxylate, sulfate, sulfonate, sulfamate, or the anion of a sulfonimide, wherein when Y is a single bond, $Z^-$ is not sulfonate. Preferably, $Z^-$ is a sulfonate or the anion of a sulfonimide, useful for effecting deprotonation of an acid deprotectable group.

Preferably, the anion $Z^-$ has the formula (II):

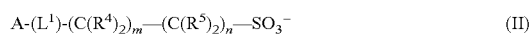

wherein A is a substituted or unsubstituted, monocyclic, polycyclic, or fused polycyclic $C_3$ or greater aliphatic groups optionally comprising O, S, N, F, or a combination comprising at least one of the foregoing, or a $C_3$ or greater aliphatic or cycloaliphatic group containing a polymerizable double or triple bond. Preferred groups A include polycyclic aliphatic groups such as adamantyl groups, norbornenyl groups, and cycloalkylenyl groups substituted with hydroxy, ester, lactone, acetyl, ketyl, or combinations of these groups.

Exemplary groups $Z^-$ include those having the following structures.

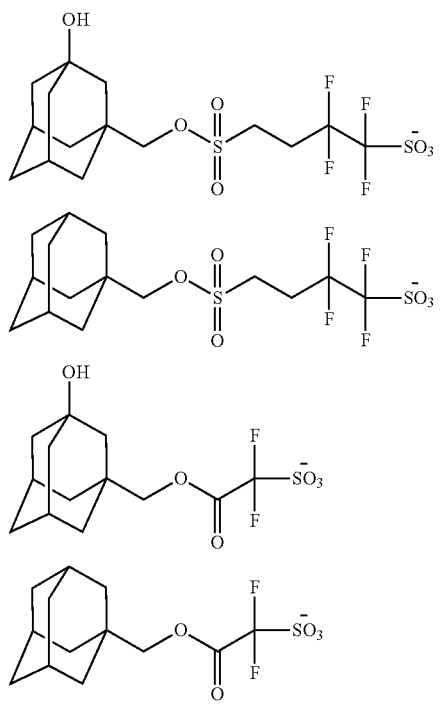

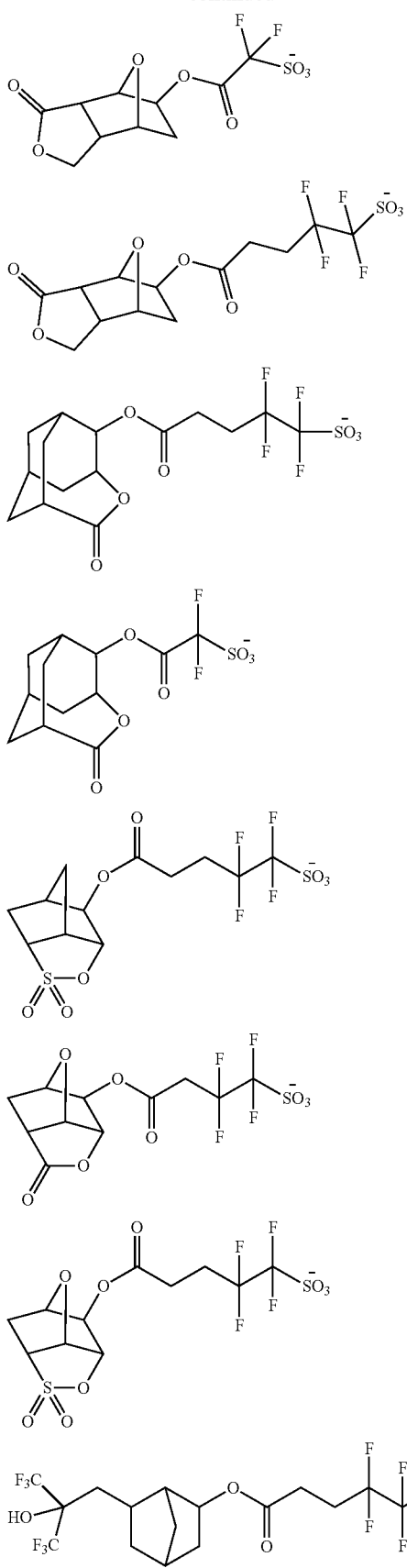
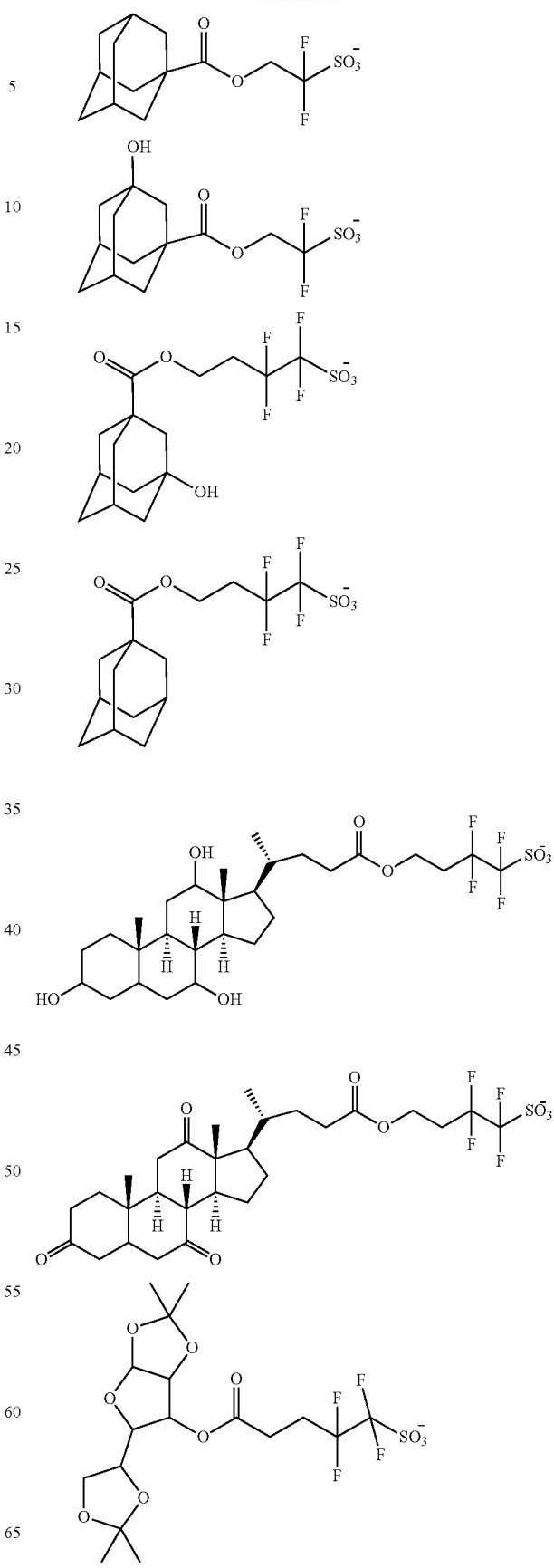

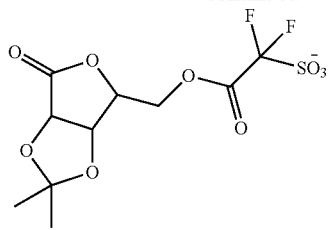
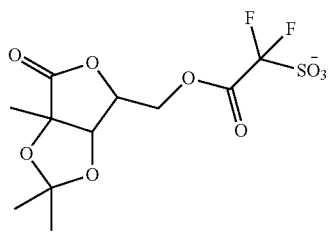
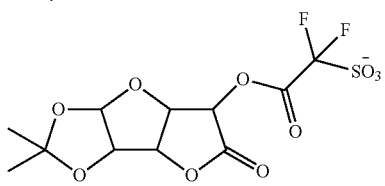
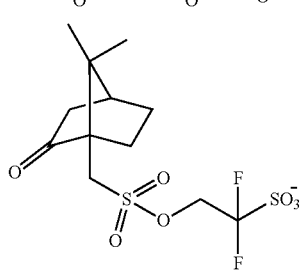
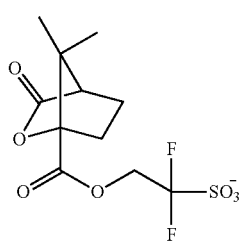
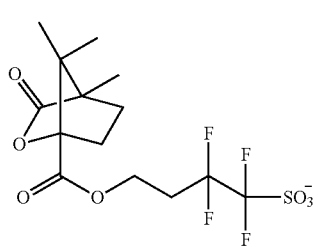
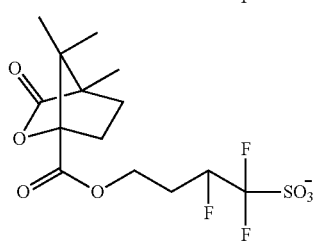
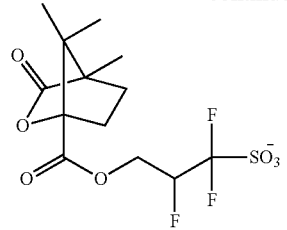

Additional exemplary groups Z⁻ include those having the following structures:

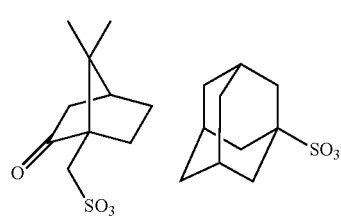
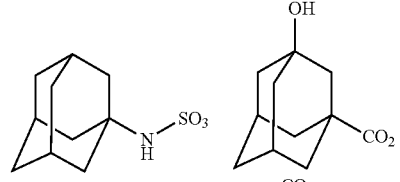
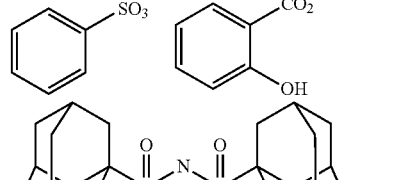

The anion Z– may also include a polymerizeable group such as a (meth)acrylate. As used herein, "(meth)acrylate means an acrylate or methacrylate. Exemplary polymerizable Z⁻ group include the following.

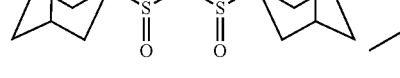
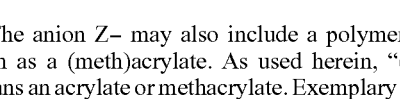
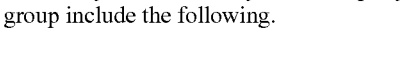
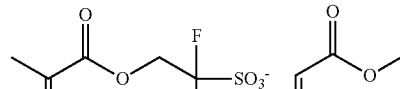
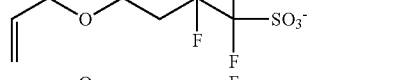
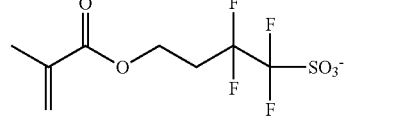

Also in formula (II), $R^4$ is H, a single bond, or a substituted or unsubstituted $C_{1-30}$ alkyl group, wherein when $R^4$ is a single bond, $R^4$ is covalently bonded to a carbon atom of A. Each $R^5$ is independently H, F, or $C_{1-4}$ fluoroalkyl, wherein at least one $R^5$ is not hydrogen. $L^1$ is a linking group comprising an —O—, —S—, —C(C=O)—, carbonate, carboxylate, sulfonate, sulfate, or a sulfonamide group. Further, m is an integer of greater than or equal to 0, preferably 0 to 10, and also preferably 1 to 5, and n is an integer of greater than or equal to 1, preferably 1 to 10, and also preferably 1 to 5.

Preferably, the photoacid generator compound includes those compounds having the formulas (Ia), (Ib), (Ic), (Id), or (Ie):

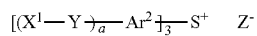
(Ia)

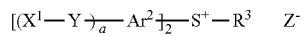
(Ib)

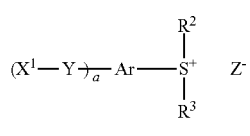
(Ic)

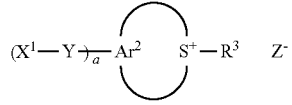
(Id)

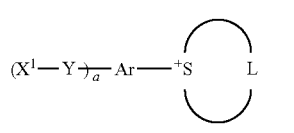
(Ie)

wherein a is an integer of from 1 to 4; $X^1$ is a $C_{3-10}$ organic group containing a fluoroalcohol or the ester of a $C_{1-20}$ perfluoroalcohol, Y is —O—, —S—, NR—, —O—C(C=O)—, —C(=O)—O—, —O—C(C=O)—O—, —OCH$_2$—(C=O)O—, —OCH$_2$C(=O)—, —SO$_2$—, —O—SO$_2$—, or a combination comprising at least one of the foregoing groups, and R is H or $C_{1-6}$ alkyl.

Also in formulas (Ia) to (Ie), $Ar^2$ is a substituted or unsubstituted phenylene, naphthylene, anthracenylene, phenanthrenylene, quinolinylene, dibenzothiophenylene, thioxanthone, thioxanthenylene, or a combination comprising at least one of the foregoing.

Each $R^2$ and $R^3$ in formula (Ic), and each $R^3$ in formulas (Ib) and (Id), is independently a substituted $C_{5-20}$ aryl not identical to Ar, or a $C_{1-20}$ alkyl. In formula (Ie), L is substituted or unsubstituted and is $C_{3-20}$ alkylene or $C_{3-20}$ cycloalkylene.

In formulas (Ia) to (Ie), $Z^-$ is as defined for formula (I).

Preferably, the photoacid generator compound has the formulas (IIIa) to (IIIg):

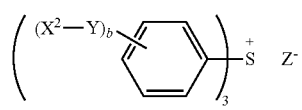
(IIIa)

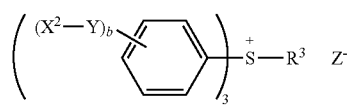
(IIIb)

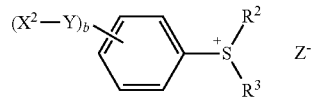
(IIIc)

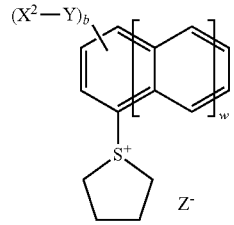
(IIId)

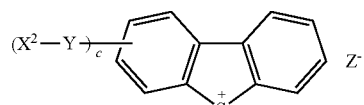
(IIIe)

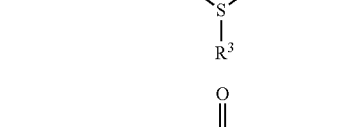
(IIIf)

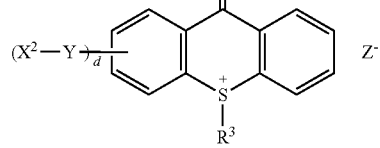
(IIIg)

wherein b is an integer of from 1 to 5, w is 0 or 1, and c, d, and e are each an integer of from 1 to 8.

In formulas (IIIa) to (IIIg), $X^2$ is a $C_{3-10}$ organic group containing a 1,1,1,3,3,3-hexafluoroisopropanol-containing group or the mono- or diester of a $C_{1-20}$ perfluoroalcohol. Furthermore, Y is —O—, —S—, NR—, —O—C(C=O)—, —C(=O)—O—, —O—C(C=O)—O—, —OCH$_2$—(C=O)O—, —OCH$_2$C(=O)—, —SO$_2$—, —O—SO$_2$—, or a combination comprising at least one of the foregoing groups, and R is H or $C_{1-6}$ alkyl.

Each $R^2$ and $R^3$ in formula (IIIc), and each $R^3$ in formula (IIIb), (IIIc), (IIIf) and (IIIg) is independently a substituted $C_{5-20}$ aryl not identical to Ar, or a $C_{1-20}$ alkyl. In formulas (IIIa)-(IIIg), $Z^-$ is as defined for formula (I).

Exemplary sulfonium cations include the following:

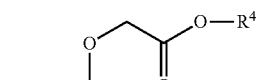
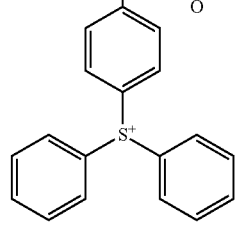

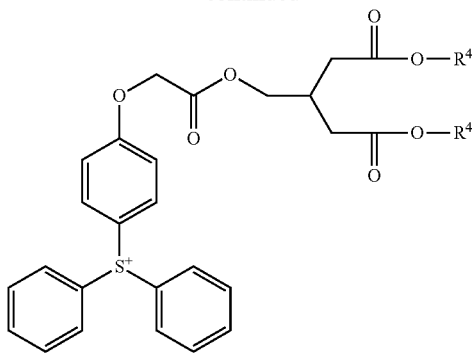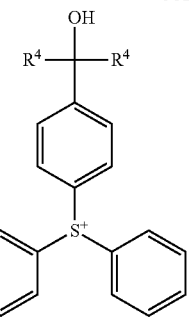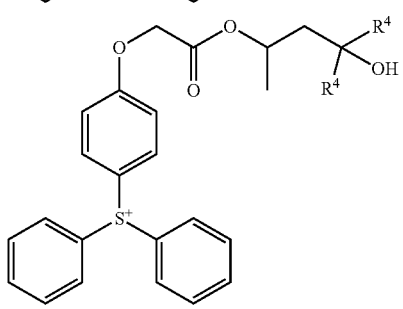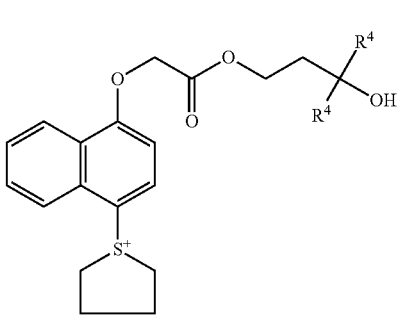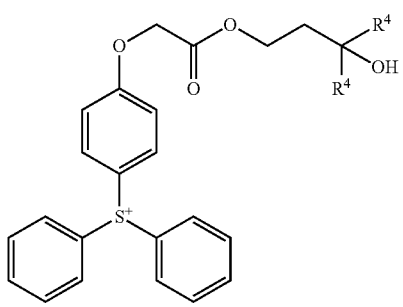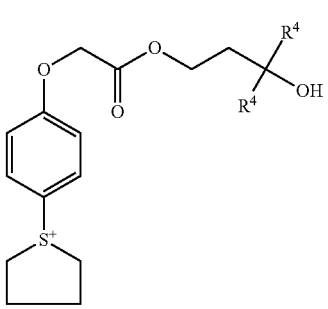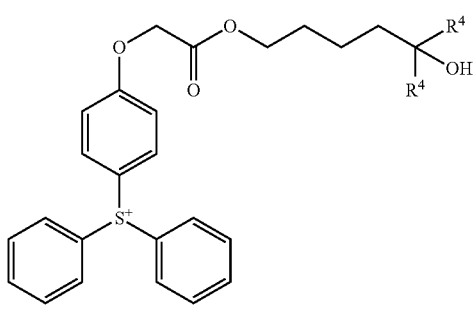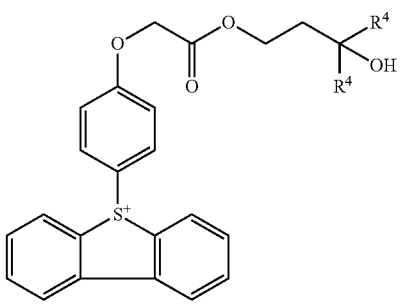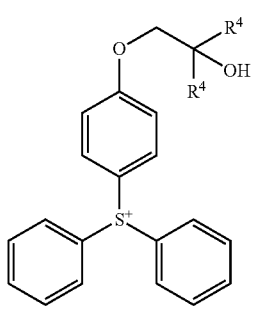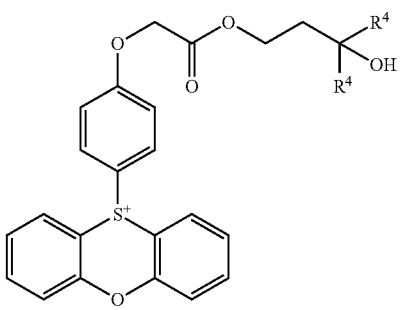

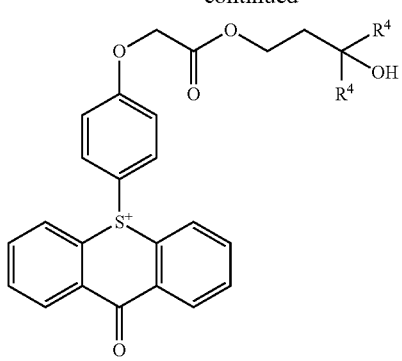

wherein R⁴ is H, F, or a $C_{1-6}$ fluoroalkyl group and at least one R⁴ is not H. Preferably, R⁴ is F or a $C_{1-4}$ perfluoroalkyl group. An exemplary group R⁴ is $CF_3$.

Exemplary PAGs include the following.

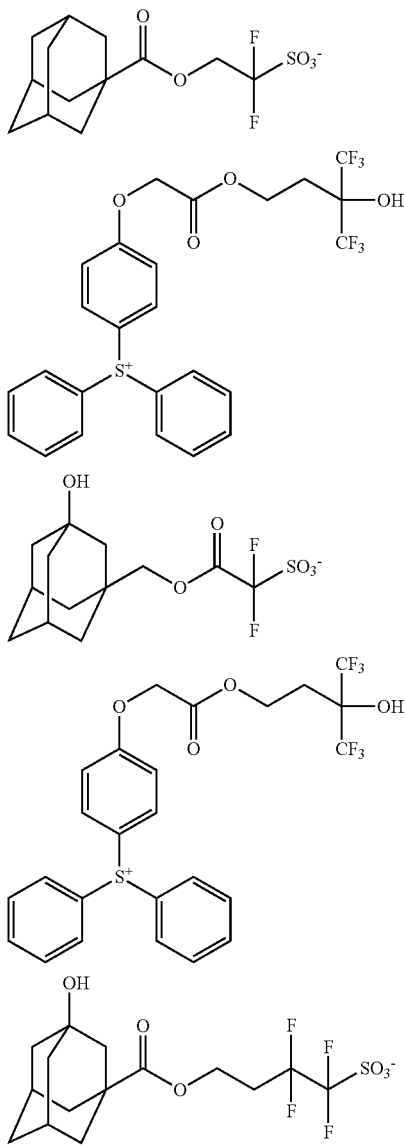

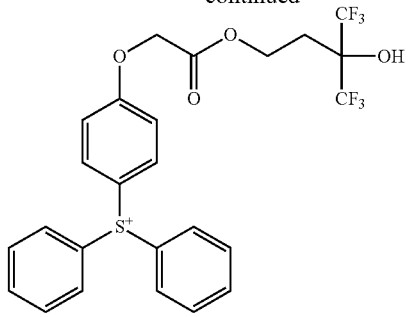

The photoacid generator including the fluorinated group hydroxy or ester containing group is prepared by any known method. For example, an alcohol of the fluorinated hydroxy or ester containing group may be attached to an aromatic ring by an ester, ether, alkylation, acylation, nucleophilic aromatic substitution, or any suitable method of attaching. Methods of forming the anion and cation are known and need not be further disclosed herein.

The photoacid generator may be formulated with or combined with a copolymer to form a photoresist. Where the combination is a polymer bound photoacid generator, an appropriately functionalized photoacid generator can be copolymerized with one or more monomers to form the copolymer, or the photoacid generator can be incorporated into the copolymer. Preferably, where the photoacid generator is incorporated into a copolymer, the photoacid generator includes a polymerizable double bond such as a (meth)acrylate, vinyl ether, norbornenyl, or other such polymerizable bond. Alternatively, or in addition, where the photoacid generator includes a vinyl ether group, linking to the copolymer may be through a ketal or acetal linkage.

Copolymers useful for forming a photoresist in combination with the photoacid generator disclosed herein include acid deprotectable monomers, base base-soluble monomers, dissolution rate modifying monomers, and etch resistant monomers. Any such monomers or combinations of monomers suitable for forming, for example, a 193 nm photoresist polymer. Preferably, a combination of monomers is used, which include a (meth)acrylate monomer having an acid deprotectable base soluble group, a (meth)acrylate monomer having a lactone functional group, a (meth)acrylate monomer having a base-soluble group not identical to that of formula (I), or a combination comprising at least one of the foregoing monomers. Other monomers, such as (meth)acrylate monomer for improving adhesion, etch resistance, etc., may also be included.

Any acid-deprotectable monomer useful for forming a 193 nm photoresist polymer may be used. Exemplary acid-deprotectable monomers include, but are not limited to:

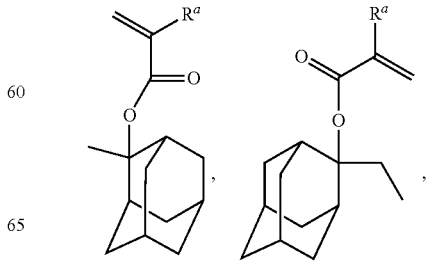

-continued

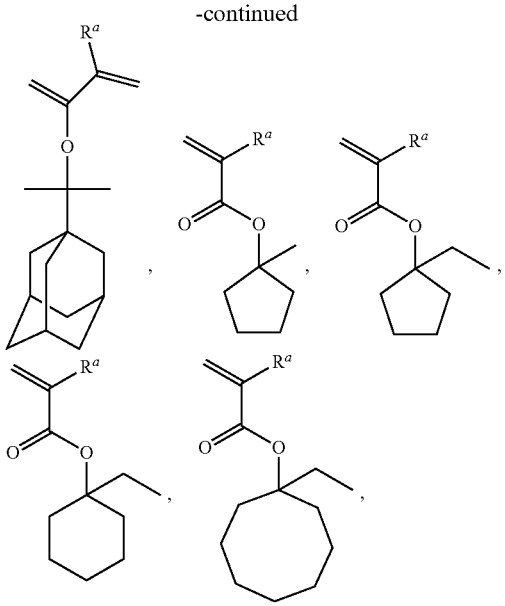

or a combination comprising at least one of the foregoing monomers, wherein $R^a$ is H, F, CN, $C_{1-10}$ alkyl, or $C_{1-10}$ fluoroalkyl.

Any lactone-containing monomer useful for forming a 193 nm photoresist polymer may be used. Exemplary such lactone-containing monomers include, but are not limited to:

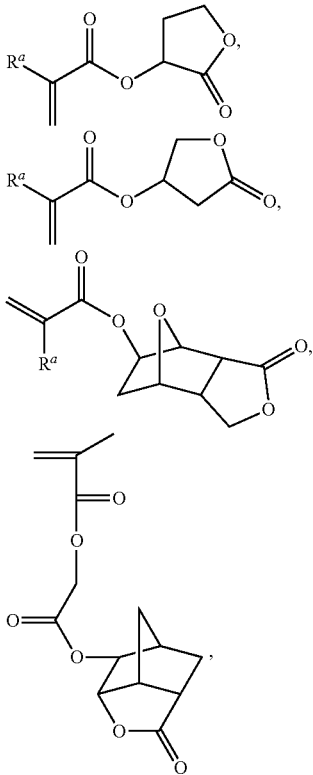

or a combination comprising at least one of the foregoing monomers, wherein $R^a$ is H, F, CN, $C_{1-10}$ alkyl, or $C_{1-10}$ fluoroalkyl.

Any base-soluble monomer useful for forming a 193 nm photoresist polymer may be used. Exemplary additional base-soluble (meth)acrylate monomers include, but are not limited to:

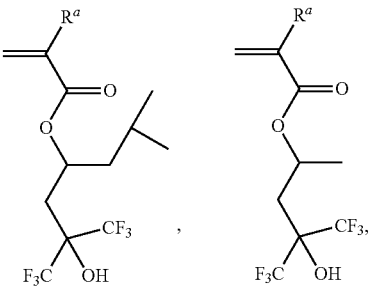

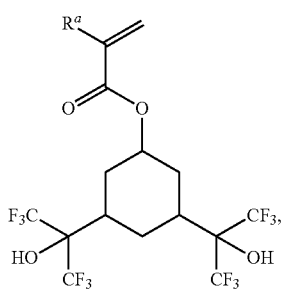

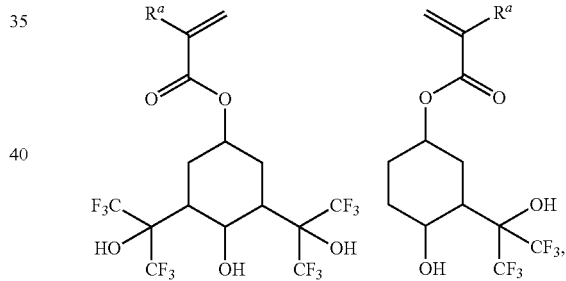

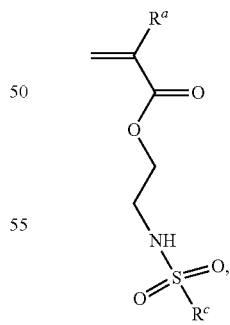

or a combination comprising at least one of the foregoing monomers, wherein $R^a$ is H, F, CN, $C_{1-10}$ alkyl, or $C_{1-10}$ fluoroalkyl, and $R^c$ is a $C_{1-4}$ perfluoroalkyl group.

The polymer may also include other monomers, including cage-structured monomers for enhancing etch resistance, with or without functional groups for improving adhesion. An exemplary adhesion-improving monomer includes:

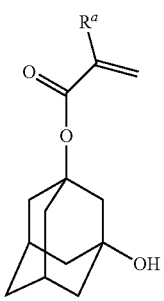

or a combination comprising the foregoing and at least one additional monomer, wherein $R^a$ is H, $C_{1-6}$ alkyl, or $CF_3$.

The photoacid generator is combined with the copolymer, either in admixture or by copolymerization, to form a photoresist. The photoresist optionally further includes a second acid sensitive polymer and/or photoacid generator, an amine or amide additive to adjust photospeed and/or acid diffusion, a solvent, and a surfactant.

The second acid-sensitive polymer may be any polymer suitable for formulating photoresists for use at 193 nm. Such acid-sensitive polymers include an acid sensitive polymer comprising acid sensitive groups and lactone-containing groups, where the acid sensitive group deprotects a base-soluble group on exposure to acid.

The photoresist composition may further an amine or amide compound, referred to herein as a quencher. Quenchers may more broadly include, for example, those based on hydroxides, carboxylates, amines, imines, and amides. In an embodiment, a useful quencher is an amine, an amide, or a combination comprising at least one of the foregoing. Preferably, such quenchers include $C_{1-30}$ organic amines, imines, or amides, or may be a $C_{1-30}$ quaternary ammonium salt of a strong base (e.g., a hydroxide or alkoxide) or a weak base (e.g., a carboxylate). Exemplary quenchers include amines such as Troger's base, a hindered amine such as diazabicycloundecene (DBU) or diazabicyclononene (DBN), N-protected amines such as N-t-butylcarbonyl-1,1-bis(hydroxymethyl)-2-hydroxyethylamine (TBOC-TRIS), or ionic quenchers including quaternary alkyl ammonium salts such as tetrabutylammonium hydroxide (TBAH) or tetrabutyl ammonium lactate.

Other components of the photoresist may include solvents and surfactants.

Solvents generally suitable for dissolving, dispensing, and coating the components include anisole, alcohols including ethyl lactate, methyl 2-hydroxybutyrate (HBM), 1-methoxy-2-propanol (also referred to as propylene glycol methyl ether, PGME), and 1-ethoxy-2 propanol, esters including n-butylacetate, 1-methoxy-2-propyl acetate (also referred to as propylene glycol methyl ether acetate, PGMEA), methoxyethoxypropionate, ethoxyethoxypropionate, and gamma-butyrolactone, ketones including cyclohexanone and 2-heptanone, and a combination comprising at least one of the foregoing solvents.

Surfactants include fluorinated and non-fluorinated surfactants, and are preferably non-ionic. Exemplary fluorinated non-ionic surfactants include perfluoro $C_4$ surfactants such as FC-4430 and FC-4432 surfactants, available from 3M Corporation; and fluorodiols such as POLYFOX PF-636, PF-6320, PF-656, and PF-6520 fluorosurfactants from Omnova.

The photoacid generator is present in the photoresist in an amount of 0.01 to 20 wt %, preferably 0.1 to 15 wt %, based on the total weight of solids. Where a polymer bound photoacid generator is used, the polymer bound photoacid generator as the corresponding monomer is present in the same amount. The copolymer may be present in an amount of 50 to 99 wt %, preferably 55 to 95 wt %, more preferably 60 to 90 wt %, and still more preferably 65 to 90 based on the total weight of solids. It will be understood that "polymer" used in this context of a component in a photoresist may mean only the copolymer disclosed herein, or a combination of the polymer with another polymer useful in a photoresist. A surfactant may be included in an amount of 0.01 to 5 wt %, preferably 0.1 to 4 wt %, and still more preferably 0.2 to 3 wt %, based on the total weight of solids. A quencher may be included in relatively small amounts of for example, from 0.03 to 5 wt % based on the total weight of solids. Other additives such as embedded barrier layer (EBL) materials for immersion lithography applications may be included in amounts of less than or equal to 30 wt %, preferably less than or equal to 20%, or more preferably less than or equal to 10%, based on the total weight of solids. The total solids content for the photoresist composition may be 0.5 to 50 wt %, preferably 1 to 45 wt %, more preferably 2 to 40 wt %, and still more preferably 5 to 35 wt %, based on the total weight of solids and solvent. It will be understood that the solids includes copolymer, photoacid generator, quencher, surfactant, and any optional additives, exclusive of solvent.

The photoresist disclosed herein may be used to form a film comprising the photoresist, where the film on the substrate constitutes a coated substrate. Such a coated substrate includes: (a) a substrate having one or more layers to be patterned on a surface thereof; and (b) a layer of the photoresist composition over the one or more layers to be patterned. Preferably, patterning is carried out using ultraviolet radiation at wavelength of less than 248 nm, and in particular, at 193 nm. The patternable film thus comprises the photoacid generator of formula (I). A method of forming an electronic device therefore includes: (a) applying a layer of a photoresist composition on a substrate; (b) patternwise exposing the photoresist composition layer to actinic radiation; and (c) developing the exposed photoresist composition layer to provide a resist relief image. Preferably, the radiation is 193 nm or 248 nm radiation.

Developing the pattern may be accomplished by either positive tone development (PTD) in which the patternwise exposed region is removed by the action of an aqueous base developer such as aqueous tetramethylammonium hydroxide (TMAH). An exemplary positive tone developer is 0.26N TMAH (aq.). Alternatively, the same patternwise exposure may be developed using an organic solvent developer to provide a negative tone development (NTD) in which the unexposed region of a pattern is removed by the action of a negative tone developer. Useful solvents for negative tone development include those also useful for dissolving, dispensing, and coating. Exemplary negative tone developer solvents include HBM, PGMEA, methoxyethoxypropionate, ethoxyethoxypropionate, and gamma-butyrolactone, cyclohexanone, 2-heptanone, and a combination comprising at least one of the foregoing solvents. A method of making a pattern thus includes pattern-wise exposing a photoresist composition layer with actinic radiation, and developing the pattern by treatment with an aqueous alkaline developer to form a positive tone relief image, or with an organic solvent developer to form a negative tone relief image.

Substrates may be any dimension and shape, and are preferably those useful for photolithography, such as silicon, silicon dioxide, silicon-on-insulator (SOI), strained silicon, gallium arsenide, coated substrates including those coated with silicon nitride, silicon oxynitride, titanium nitride, tantalum nitride, ultrathin gate oxides such as hafnium oxide, metal or metal coated substrates including those coated with titanium, tantalum, copper, aluminum, tungsten, alloys thereof, and combinations thereof. Preferably, the surfaces of substrates herein include critical dimension layers to be patterned including, for example, one or more gate-level layers or other critical dimension layer on the substrates for semiconductor manufacture. Such substrates may preferably include silicon, SOI, strained silicon, and other such substrate materials, formed as circular wafers having dimensions such as, for example, 200 mm, 300 mm, or larger in diameter, or other dimensions useful for wafer fabrication production.

The invention is further illustrated by the following examples. All compounds and reagents used herein are available commercially except where a procedure is provided below. 4-(2-ter-(1-ethylcyclopentylpxy)-2-oxoethoxy)phenyldiphenylsulfonium bromide was obtained from WAKO Chemicals. 1,1,1-trifluoro-2-trifluoromethyl-2,4-butanediol (Compound 4) was obtained from Halocarbon Products Corporation. PAG-B1, identified below was obtained from Central Glass Co., Ltd. PAG-B2 was obtained from Daychem Laboratories, Inc.

Photoacid generator PAG-A1 was prepared by the synthetic scheme outlined in Synthesis Scheme 1.

A suspension of 4-(2-ter-(1-ethylcyclopentyloxy)-2-oxoethoxy)phenyldiphenylsulfonium bromide (30 g, 58.42 mmol) in 200 mL of 5% (w/w) aqueous solution of hydrochloric acid was stirred at room temperature for 16 h. The mixture was washed twice with 100 mL of methyl t-butyl ether. The resulting aqueous which contained compound 1 was added triethylammonium 2-(adamantane-1-carbonyloxy)-1,1-difluoroethan-1-sulfonate (Compound 2; 21.2 g, 50 mmol) and 200 mL methylene chloride and the mixture stirred at room temperature for 16 h. The lower organic phase was separated from the aqueous phase and washed with deionized water (4×200 mL). The organic phase was concentrated under reduced pressure to produce 27.7 g of the crude product (Compound 3) which was used subsequently without further purification.

To a solution of Compound 3 (15.5 g, 22.90 mmol) in 150 mL of anhydrous tetrahydrofuran (THF) was added carbonyldiimidazole (CDI, 2.5 g, 15.4 mmol) portion-wise over a 30 min period. After the addition was completed the reaction was stirred at room temperature for 2 hr. The mixture was then heated to reflux and then Compound 4 (3.3 g, 15.6 mmol) was added portion-wise over a 5 min period. The reaction mixture was stirred at 67° C. overnight. The resulting amber solution was cooled to 25° C. and the THF was removed under reduced pressure. The resulting residue was dissolved in 100 mL of dichloromethane and washed with 0.1N of HCl (100 mL) followed by washing with water (4×200 mL). The organic phase was separated and washed with deionized water (5×50 mL). The organic phase was separated, concentrated and poured into methyl t-butyl ether to precipitate the target photoacid generator PAG-A1. The isolated yield was 7.3 g (56%). Samples of the PAG were assayed for purity by HPLC-MS. The cation was determined to be 98.0% pure as detected by UV at 230 nm, and purity detected by positive ion mass spectrometry is 99.3%. The anion purity as measured by

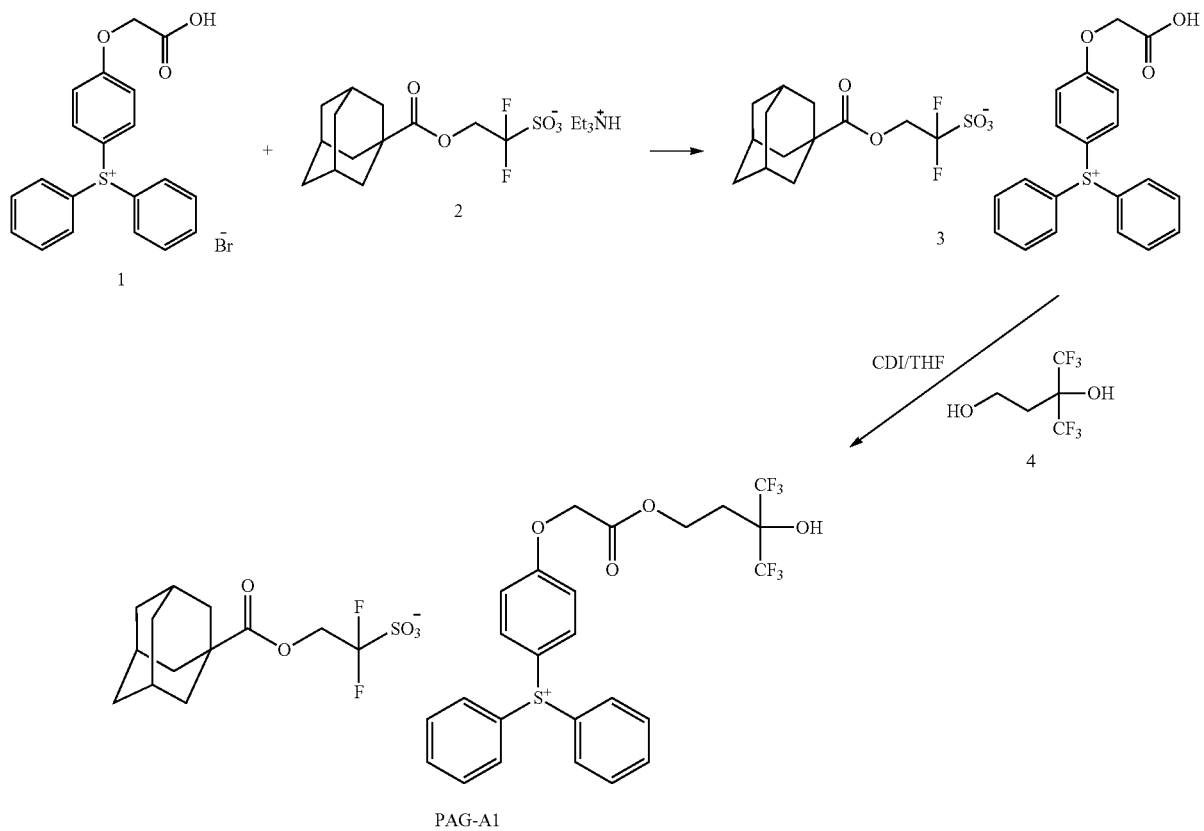

Synthesis Scheme 1 negative ion liquid chromatography mass spectrometry (LCMS) was determined to be 99.3%.

Photoacid generator PAG-A2 was prepared by the synthetic scheme outlined in Synthesis Scheme 2.

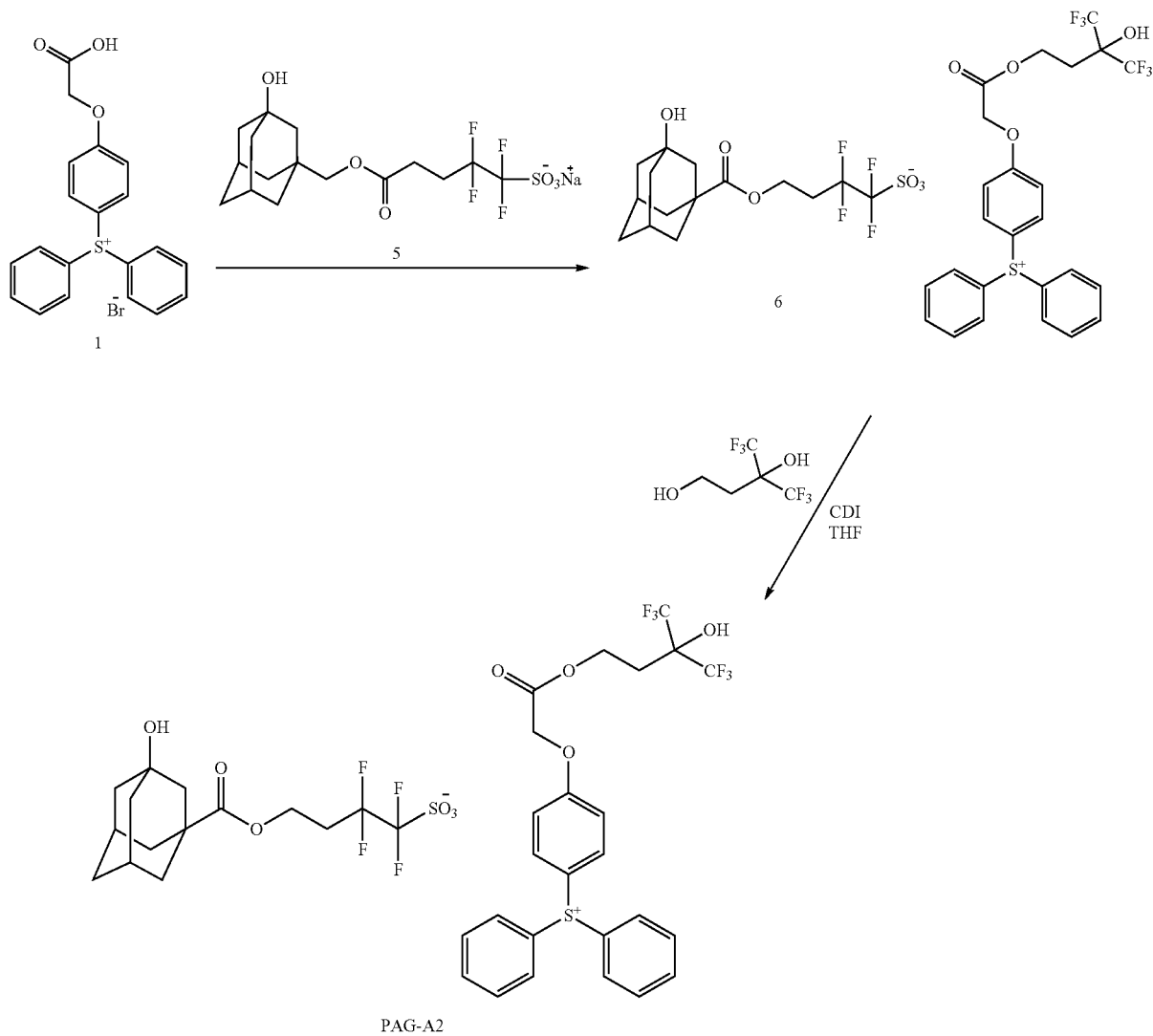

Synthesis Scheme 2

PAG-A2

A suspension of 4-(2-ter-(1-ethylcyclopentyloxy)-2-oxoethoxy)phenyldiphenylsulfonium bromide (30 g, 58.42 mmol) in 200 mL of 5% (w/w) aqueous solution of hydrochloric acid was stirred at room temperature for 16 h. The mixture was washed twice with 100 mL of methyl t-butyl ether. To the resulting aqueous phase which contained compound 1 was added sodium 1,1,2,2-tetrafluoro-5-(((1r,3s,5R,7S)-3-hydroxyadamantan-1-yl)methoxy)-5-oxopentane-1-sulfonate (Compound 5; 25.7 g, 58.4 mmol) and 200 mL methylene chloride and the mixture stirred at room temperature for 16 h. The lower organic phase was separated from the aqueous phase and washed with deionized water (4×200 mL). The organic phase was concentrated under reduced pressure to produce 28.2 g of the crude product (Compound 6) which was used subsequently without further purification.

To a solution of Compound 6 (30 g, 40.49 mmol) in 150 mL of anhydrous tetrahydrofuran (THF) was added carbonyldiimidazole (CDI, 6.5 g, 40.12 mmol) portion-wise over a 30 min. period. After the addition was completed the reaction was stirred at room temperature for 2 hr. The mixture was heated to reflux and then Compound 4 (8.5 g, 40.10 mmol) was added portion-wise over a 5 min period. The reaction mixture was stirred at 67° C. overnight. The resulting amber solution was cooled to 25° C. and the THF was removed under reduced pressure. The resulting residue was dissolved in 100 mL of dichloromethane and washed with 0.1N of HCl (100 mL) followed by washing with water (4×200 mL). The organic phase was separated and washed with deionized water (5×50 mL). The organic phase was separated, concentrated and poured into heptanes to precipitate the target PAG-A2. The crude PAG-A2 was suspended in methyl t-butyl ether and the suspension was stirred at room temperature for 30 minutes, Methyl t-butyl ether was decanted and the target product was dried under vacuum. Yield was 15.0 g (40%). Samples of the PAG were assayed for purity by HPLC-MS. The cation was determined to be 98.5% pure as detected by UV at 230 nm, and 100% pure as detected by positive ion mass spectrometry. The anion purity as measured by negative ion liquid chromatography mass spectrometry (LCMS) was determined to be 100%.

The solubility of several different photoacid generators was determined in 0.26 N aqueous tetramethylammonium hydroxide (TMAH) developer. Solubility of each of the compounds PAG-A1, PAG-A2, PAG-B1 and PAG-B2 was tested in positive tone developer (PTD) 0.26 N aqueous tetramethylammonium hydroxide (TMAH). Only PAG-A1 and PAG-A2 (each with hexafluoroalcohol substituent groups) were soluble in TMAH, at 2 wt %. The reference compounds PAG-B1 and PAG-B2 are insoluble in TMAH, at 2 wt %. Hence, onium cations with hexafluoroalcohol substituents provide PTD-developer soluble PAGs.

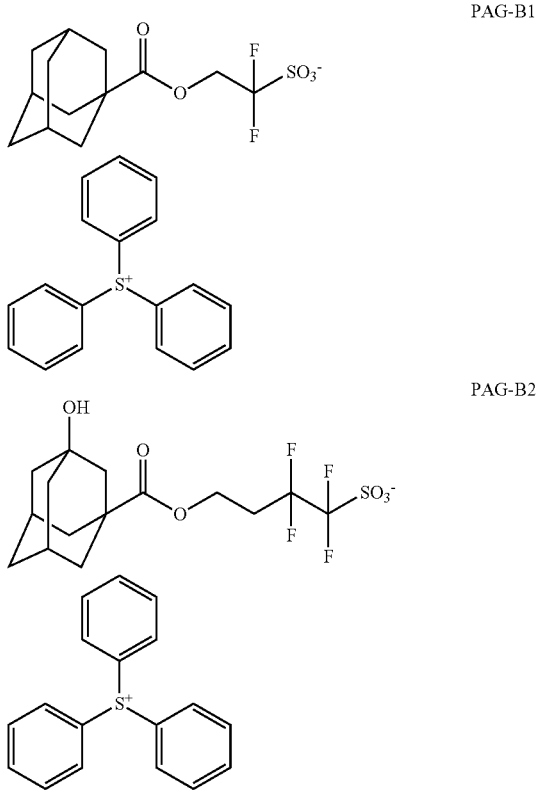

The photoacid generators were also evaluated for solubility in a selection of organic solvents useful for negative tone photoresist development and formulation. Solubility of each of the compounds PAG-A1, PAG-A2, PAG-B1 and PAG-B2 were obtained for attempts to completely dissolve the PAG at 2 wt % at room temperature in different organic solvents or solvent blends. The results for the solubility tests (i.e., where the PAG is observed to be completely soluble in the solvent, or is only partially soluble or insoluble based on the presence of insoluble material) are shown in Table 1.

TABLE 1

|    | PAG-A1 | PAG-B1 | PAG-A2 | PAG-B2 |
|----|--------|--------|--------|--------|
| S1 | ○      | X      | ○      | X      |
| S2 | ○      | X      | ○      | X      |
| S3 | ○      | X      | ○      | X      |
| S4 | ○      | X      | ○      | X      |

TABLE 1-continued

|    | PAG-A1 | PAG-B1 | PAG-A2 | PAG-B2 |
|----|--------|--------|--------|--------|

S1: Propylene glycol monomethyl ether acetate (PGMEA)
S2: 2-Heptanone
S3: 1:1 (w/w) blend of 2-heptanone:n-butylpropionate
S4: n-butylacetate (NBA)
○: compound soluble at 2 wt %
X: compound is partially soluble or insoluble.

As seen in Table 1, PAG compounds including hexafluoroalcohol substituents are generally soluble in solvents at concentrations useful for formulation and in negative tone developers. The inclusion of a hexafluoroalcohol group on the cationic portion of the PAG thus increases solubility of the PAG cation/anion pair in both highly polar aqueous (basic) and in a range of organic solvents having different polarities.

Lithographic evaluation of the exemplary PAG was carried out according to the following procedure. Photoresists were formulated using the components and proportions shown in Table 2. A commercial photoresist polymer (obtained from Dow Electronic Materials) was used in all examples. The photoresist polymer is a pentapolymer incorporating monomers M1, M2, M3, M4 and M5, where the mole percentage of M1/M2/M3/M4/M5 is 20/20/30/20/10 for a total of 100 mole percent of monomers. The Mw of the polymer was 8,000 g/mol.

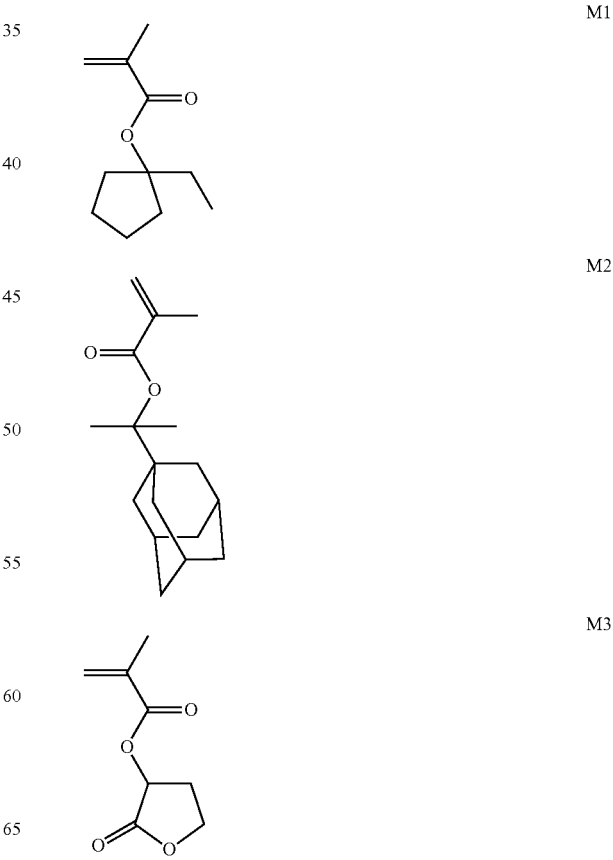

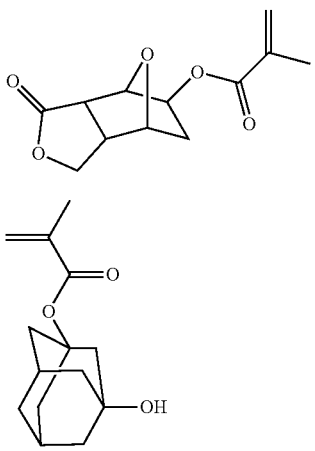

M4

M5

The PAG (see Table 2), base (t-butyloxycarbonyl-4-hydroxypyridine, TBOC-4HP), and surface leveling agent (PF 656 surfactant, available from Omnova), are given as weight percent based on 100% solids content, with the balance of the solids being the polymer. Propylene glycol monomethyl ether acetate (S1) and methyl-2-hydroxyisobutyrate (S5) were included as the solvents. The weight ratio of solvent S1:S5 in the final formulation was 1:1. The final percent solids in each of the Comparative Examples 1 and 2, and in the Example, was 4 wt %.

Photoresist formulation compositions for Comparative Example and Examples 1 and 2 are shown in Table 2 below:

TABLE 2

| Photoresist | PAG | PAG (wt %) | Base (wt %) | SLA (wt %) |
|---|---|---|---|---|
| Comparative Example 1 | Triphenylsulfonium perfluorobutane-sulfonate | 9.56 | 1.03 | 0.1 |
| Comparative Example 2 | PAG-2 | 10.27 | 1.03 | 0.1 |
| Example | PAG-1A | 14.57 | 1.03 | 0.1 |

The above photoresists were lithographically processed as follows. The photoresist was spin coated onto a 200 mm silicon wafer having 84 nm of an organic antireflective coating (AR™77, Dow Electronic Materials) and baked at 110° C. for 60 seconds, to form a resist film 100 nm in thickness. The photoresist was exposed with ArF excimer laser (193 nm) through a mask pattern targeting a line and space pattern (L/S pattern) having a line width of 90 nm and a pitch of 180 nm, using an ArF exposure apparatus ASML-1100 (manufactured by ASML), NA (numerical aperture)=0.75 under annular illumination with outer/inner sigma of 0.89/0.64 with focus offset/step 0.10/0.05. The wafers were post exposure baked (PEB) at 100° C. for 60 seconds followed by developing with 0.26 N aqueous tetramethylammonium hydroxide (TMAH) developer and subsequent water wash.

In each example, an L/S pattern having a line width of 90 nm and a pitch of 180 nm was formed. Mask Error Factor (MEF) and Line Width Roughness (LWR) was determined by processing the image captured by top-down scanning electron microscopy (SEM) using a Hitachi 9380 CD-SEM, operating at an accelerating voltage of 800 volts (V), probe current of 8.0 picoamperes (pA), using 200 K× magnification. Mask Error Factor (MEF) was defined as the ratio of CD change on the resolved resist pattern to the relative dimension change on the mask pattern.

The results from the lithographic evaluation of the above photoresist formulations are shown in Table 3.

TABLE 3

| Photoresist | $E_{size}$ (mJ/cm$^2$) | MEF | LWR |
|---|---|---|---|
| Comparative Example 1 | 24.15 | 4.02 | 12.1 |
| Comparative Example 2 | 29.10 | 3.50 | 11.2 |
| Example | 38.70 | 3.35 | 10.7 |

As seen in Table 3, the Example, which includes PAG-A1, showed improved lithographic performance of improved mask error factor (3.35 for Ex. relative to CEx1 with 4.02 and CEx2 with 3.55) and improved line width Roughness (10.7 for Ex. relative to CEx1 with 12.1 and CEx2 with 11.2).

All ranges disclosed herein are inclusive of the endpoints, and the endpoints are independently combinable with each other. The suffix "(s)" as used herein is intended to include both the singular and the plural of the term that it modifies, thereby including at least one of that term. "Optional" or "optionally" means that the subsequently described event or circumstance can or cannot occur, and that the description includes instances where the event occurs and instances where it does not. As used herein, "combination" is inclusive of blends, mixtures, alloys, or reaction products. All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. Further, it should further be noted that the terms "first," "second," and the like herein do not denote any order, quantity, or importance, but rather are used to distinguish one element from another.

The invention claimed is:

1. A compound having the formula (I):

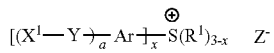

wherein a is an integer of from 1 to 10, and x is an integer of from 1 to 3, $X^1$ comprises a fluoroalcohol or fluorinated anhydride, Y is a single bond, $C_{1-20}$ alkylene group, O, S, NR, ester, carbonate, sulfonate, sulfone, or sulfonamide, wherein R is H or $C_{1-20}$ alkyl, and wherein the $C_{1-20}$ alkylene group is structurally only carbon, or one or more structural carbon atoms in the $C_{1-20}$ alkylene group is replaced by oxygen, carbonyl, ester, or a combination comprising at least one of the foregoing, Ar is a substituted or unsubstituted, $C_5$ or greater monocyclic, polycyclic, or fused polycyclic cycloalkyl; or a substituted or unsubstituted, $C_5$ or greater monocyclic, polycyclic, or fused polycyclic aryl group, wherein the cycloalkyl or aryl is a carbocycle or comprises a heteroatom comprising O, S, N, F, or a combination comprising at least one of the foregoing, each $R^1$ is independently a substituted $C_{5-40}$ aryl, substituted $C_{5-40}$ heteroaryl, $C_{1-40}$ alkyl, a $C_{3-40}$ cycloalkyl, wherein when x is 1, the two groups $R^1$ are separate or bonded to each other to form a $C_{4-40}$ ring structure, and Z⁻ is a carboxylate, sulfate, sulfonate, sulfamate or the anion of a sulfonimide, wherein when Y is a single bond, Z⁻ is not sulfonate.

2. The compound of claim 1, wherein a is an integer of from 1 to 4, x is 1, $X^1$ is a 1,1,1,3,3,3-hexafluoroisopropanol-containing group, and Y is —O—, —S—, NR—, —O—C(=O)—, —C(=O)—O—, —O—C(=O)—O—, —OCH$_2$—(C=O)O—, —OCH$_2$C(=O)—, —SO$_2$—, —O—SO$_2$—, or a combination comprising at least one of the foregoing groups, wherein R is H or $C_{1-6}$ alkyl.

3. The compound of claim 1, wherein Ar is a substituted or unsubstituted phenylene, naphthylene, anthracenylene, phenanthrenylene, quinolinylene, dibenzothiophenylene, thioxanthone, thiooxaanthracenylene, or a combination comprising at least one of the foregoing.

4. The compound of claim 1, wherein $R^1$ is independently a substituted $C_{5-20}$ aryl or a $C_{1-20}$ alkyl, wherein when x is 1, the two groups $R^1$ are separate or bonded to each other to form a $C_{4-20}$ ring structure.

5. The compound of claim 1, the compound having the formulas (Ia), (Ib), (Ic), (Id), or (Ie):

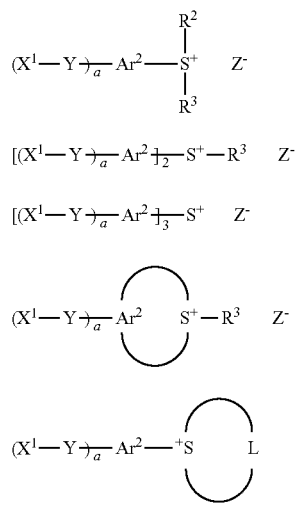

wherein a is an integer of from 1 to 4;
$X^1$ is a $C_{3-10}$ organic group containing a fluoroalcohol, Y is —O—, —S—, NR—, —O—C(=O)—, —C(=O)—O—, —O—C(=O)—O—, —OCH$_2$—(C=O)O—, —OCH$_2$C(=O)—, —SO$_2$—, —O—SO$_2$—, or a combination comprising at least one of the foregoing groups, and R is H or $C_{1-6}$ alkyl,
$Ar^2$ is a substituted or unsubstituted phenylene, naphthylene, anthracenylene, phenanthrenylene, quinolinylene, dibenzothiophenylene, thioxanthone, thioxanthenylene, or a combination comprising at least one of the foregoing,
each $R^2$ and $R^3$ is independently a substituted $C_{5-20}$ aryl not identical to Ar, or a $C_{1-20}$ alkyl, and L is a substituted or unsubstituted $C_{2-20}$ alkylene, and
Z⁻ is a sulfate, sulfonate, or the anion of a sulfonimide.

6. The compound of claim 1, comprising the formulas (IIIa) to (IIIg):

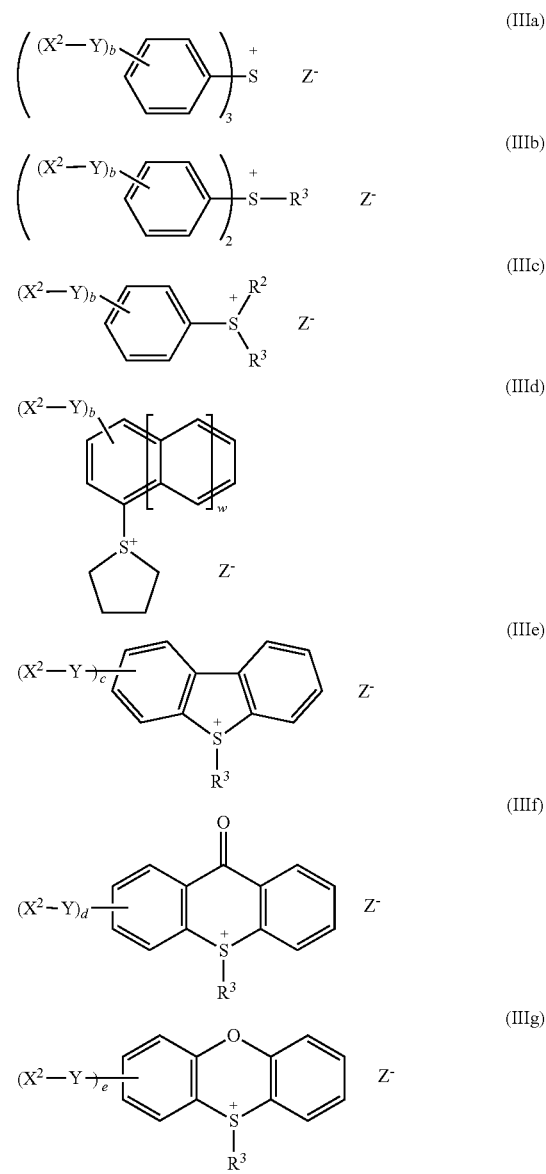

wherein b is an integer of from 1 to 5, w is 0 or 1, and c, d, and e are each an integer of from 1 to 8;
$X^2$ is a $C_{3-10}$ organic group containing a 1,1,1,3,3,3-hexafluoroisopropanol-containing group,
Y is —O—, —S—, NR—, —O—C(=O)—, —C(=O)—O—, —O—C(=O)—O—, —OCH$_2$—(C=O)O—, —OCH$_2$C(=O)—, —SO$_2$—, —O—SO$_2$—, or a combination comprising at least one of the foregoing groups, and R is H or $C_{1-6}$ alkyl,
each $R^2$ and $R^3$ is independently a substituted $C_{5-20}$ aryl not identical to Ar, or a $C_{1-20}$ alkyl, and L is a substituted or unsubstituted $C_{2-20}$ alkylene, and
Z⁻ is a carboxylate, sulfate, sulfonate, sulfamate, or the anion of a sulfonimide.

7. The compound of claim 1, wherein Z⁻ has the formula (II):

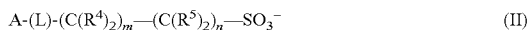

wherein
A is a substituted or unsubstituted, monocyclic, polycyclic, or fused polycyclic $C_3$ or greater cycloaliphatic group optionally comprising O, S, N, F, or a combination comprising at least one of the foregoing, or a $C_3$ or greater aliphatic or cycloaliphatic group containing a polymerizable double or triple bond, $R^4$ is H, a single bond, or a substituted or unsubstituted $C_{1-30}$ alkyl group, wherein when $R^4$ is a single bond, $R^4$ is covalently bonded to a carbon atom of A, each $R^5$ is independently H, F, or $C_{1-4}$ fluoroalkyl, wherein at least one $R^5$ is not hydrogen, L is a linking group comprising an —O—, —S—, —C(=O)—, carbonate, carboxylate, sulfonate, sulfate, or a sulfonamide group, and q is an integer of 0 to 10, m is an integer of greater than or equal to 0, and n is an integer of greater than or equal to 1.

8. A photoresist composition, comprising the compound of claim 1 and a polymer having acid labile protecting groups.

9. A coated substrate, comprising: (a) a substrate having one or more layers to be patterned on a surface thereof; and (b) a layer of a photoresist composition of claim 8 over the one or more layers to be patterned.

10. The photoresist composition of claim 8, wherein a is an integer of from 1 to 4, x is 1, $X^1$ is a 1,1,1,3,3,3-hexafluoroisopropanol-containing group, and Y is —O—, —S—, NR—, —O—C(=O)—, —C(=O)—O—, —O—C(=O)—O—, —OCH$_2$—(C=O)O—, —OCH$_2$C(=O)—, —SO$_2$—, —O—SO$_2$—, or a combination comprising at least one of the foregoing groups, wherein R is H or $C_{1-6}$ alkyl.

11. The photoresist composition of claim 8, wherein the compound has one of formulas (Ia), (Ib), (Ic), (Id), or (Ie):

$$(X^1-Y)_a-Ar^2-\overset{R^2}{\underset{R^3}{S^+}} \quad Z^- \qquad \text{(Ia)}$$

$$[(X^1-Y)_a-Ar^2]_2-S^+-R^3 \quad Z^- \qquad \text{(Ib)}$$

$$[(X^1-Y)_a-Ar^2]_3-S^+ \quad Z^- \qquad \text{(Ic)}$$

$$(X^1-Y)_a-Ar^2 \underset{\smile}{\overset{\frown}{S^+}}-R^3 \quad Z^- \qquad \text{(Id)}$$

$$(X^1-Y)_a-Ar^2-{}^+S\underset{\smile}{\overset{\frown}{\ }}L \quad Z^- \qquad \text{(Ie)}$$

wherein a is an integer of from 1 to 4;

$X^1$ is a $C_{3-10}$ organic group containing a fluoroalcohol, Y is —O—, —S—, NR—, —O—C(=O)—, —C(=O)—O—, —O—C(=O)—O—, —OCH$_2$—(C=O)O—, —OCH$_2$C(=O)—, —SO$_2$—, —O—SO$_2$—, or a combination comprising at least one of the foregoing groups, and R is H or $C_{1-6}$ alkyl, $Ar^2$ is a substituted or unsubstituted phenylene, naphthylene, anthracenylene, phenanthrenylene, quinolinylene, dibenzothiophenylene, thioxanthone, thioxanthenylene, or a combination comprising at least one of the foregoing, each $R^2$ and $R^3$ is independently a substituted $C_{5-20}$ aryl not identical to Ar, or a $C_{1-20}$ alkyl, and L is a substituted or unsubstituted $C_{2-20}$ alkylene, and $Z^-$ is a sulfate, sulfonate, or the anion of a sulfonimide.

12. The photoresist composition of claim 8, wherein the compound has one of formulas (IIIa) to (IIIg):

$$\left((X^2-Y)_b-\text{Ar}\right)_3-S^+ \quad Z^- \qquad \text{(IIIa)}$$

$$\left((X^2-Y)_b-\text{Ar}\right)_2-S^+-R^3 \quad Z^- \qquad \text{(IIIb)}$$

$$(X^2-Y)_b-\text{Ar}-\overset{R^2}{\underset{R^3}{S^+}} \quad Z^- \qquad \text{(IIIc)}$$

(IIId) naphthalene-tetrahydrothiophenium structure with $(X^2-Y)_b$ substituent and $Z^-$ (IIIe) dibenzothiophenium structure with $(X^2-Y)_c$ and $R^3$ on S, $Z^-$ (IIIf) thioxanthonium structure with $(X^2-Y)_d$ and $R^3$ on S, $Z^-$ (IIIg) phenoxathiinium structure with $(X^2-Y)_e$ and $R^3$ on S, $Z^-$ wherein b is an integer of from 1 to 5, w is 0 or 1, and c, d, and e are each an integer of from 1 to 8;

$X^2$ is a $C_{3-10}$ organic group containing a 1,1,1,3,3,3-hexafluoroisopropanol-containing group, Y is —O—, —S—, NR—, —O—C(=O)—, —C(=O)—O—, —O—C(=O)—O—, —OCH$_2$—(C=O)O—, —OCH$_2$C(=O)—, —SO$_2$—, —O—SO$_2$—, or a combination comprising at least one of the foregoing groups, and R is H or $C_{1-6}$ alkyl, each $R^2$ and $R^3$ is independently a substituted $C_{5-20}$ aryl not identical to Ar, or a $C_{1-20}$ alkyl, and L is a substituted or unsubstituted $C_{2-20}$ alkylene, and $Z^-$ is a carboxylate, sulfate, sulfonate, sulfamate, or the anion of a sulfonimide.

13. The photoresist composition of claim 8, wherein $Z^-$ has the formula (II):

$$\text{A-(L)-(C}(R^4)_2)_m-(C(R^5)_2)_n-\text{SO}_3^- \qquad \text{(II)}$$

wherein

A is a substituted or unsubstituted, monocyclic, polycyclic, or fused polycyclic $C_3$ or greater cycloaliphatic group optionally comprising O, S, N, F, or a combination comprising at least one of the foregoing, or a $C_3$ or greater aliphatic or cycloaliphatic group containing a polymerizable double or triple bond, $R^4$ is H, a single bond, or a substituted or unsubstituted $C_{1-30}$ alkyl group, wherein when $R^4$ is a single bond, $R^4$ is covalently bonded to a carbon atom of A, each $R^5$ is independently H, F, or $C_{1-4}$ fluoroalkyl, wherein at least one $R^5$ is not hydrogen, L is a linking group comprising an —O—, —S—, —C(=O)—, carbonate, carboxylate, sulfonate, sulfate, or a sulfonamide group, and q is an integer of 0 to 10, m is an integer of greater than or equal to 0, and n is an integer of greater than or equal to 1.

14. The compound of claim 1, wherein $X^1$ is a 1,1,1,3,3,3-hexafluoroisopropanol-containing group.

15. A method of making a relief image, comprising
coating a substrate with a photoresist layer comprising
a polymer having acid deprotectable groups, and
a compound having the formula (I):

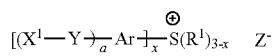

wherein a is an integer of from 1 to 10, and x is an integer of from 1 to 3, $X^1$ comprises a fluoroalcohol or fluorinated anhydride, Y is a single bond, $C_{1-20}$ alkylene group, O, S, NR, ester, carbonate, sulfonate, sulfone, or sulfonamide, wherein R is H or $C_{1-10}$ alkyl, and wherein the $C_{1-20}$ alkylene group is structurally only carbon, or one or more structural carbon atoms in the $C_{1-20}$ alkylene group is replaced by oxygen, carbonyl, ester, or a combination comprising at least one of the foregoing, Ar is a substituted or unsubstituted, $C_5$ or greater monocyclic, polycyclic, or fused polycyclic cycloalkyl; or a substituted or unsubstituted, $C_5$ or greater monocyclic, polycyclic, or fused polycyclic aryl group, wherein the cycloalkyl or aryl is a carbocycle or comprises a heteroatom comprising O, S, N, F, or a combination comprising at least one of the foregoing, each $R^1$ is independently a substituted $C_{5-40}$ aryl, substituted $C_{5-40}$ heteroaryl, $C_{1-40}$ alkyl, a $C_{3-40}$ cycloalkyl, wherein when x is 1, the two groups $R^1$ are separate or bonded to each other to form a $C_{4-40}$ ring structure, and $Z^-$ is a carboxylate, sulfate, sulfonate, sulfamate, or the anion of a sulfonimide, wherein when Y is a single bond, $Z^-$ is not sulfonate;

patternwise exposing the photoresist composition layer to actinic radiation; and developing the pattern by treatment with an aqueous alkaline developer to form a positive tone relief image, or with an organic solvent developer to form a negative tone relief image.

16. The method of making a relief image of claim 15, wherein $X^1$ is a 1,1,1,3,3,3-hexafluoroisopropanol-containing group.

17. The method of claim 15, wherein a is an integer of from 1 to 4, x is 1, $X^1$ is a 1,1,1,3,3,3-hexafluoroisopropanol-containing group, and Y is —O—, —S—, NR—, —O—C(=O)—, —C(=O)—O—, —O—C(=O)—O—,
—OCH$_2$—(C=O)O—, —OCH$_2$C(=O)—, —SO$_2$—, —O—SO$_2$—, or a combination comprising at least one of the foregoing groups, wherein R is H or $C_{1-6}$ alkyl.

18. The method of claim 15, wherein the compound has one of formulas (Ia), (Ib), (Ic), (Id), or (Ie):

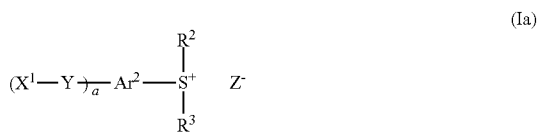

(Ia)

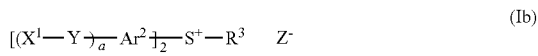

(Ib)

(Ic)

(Id)

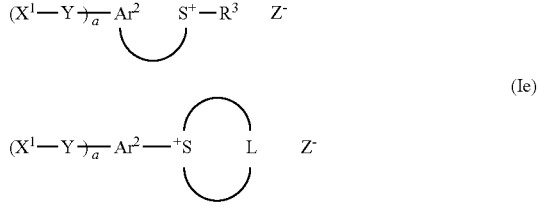

(Ie)

wherein a is an integer of from 1 to 4;

$X^1$ is a $C_{3-10}$ organic group containing a fluoroalcohol, Y is —O—, —S—, NR—, —O—C(=O)—, —C(=O)—O—, —O—C(=O)—O—, —OCH$_2$—(C=O)O—, —OCH$_2$C(=O)—, —SO$_2$—, —O—SO$_2$—, or a combination comprising at least one of the foregoing groups, and R is H or $C_{1-6}$ alkyl, $Ar^2$ is a substituted or unsubstituted phenylene, naphthylene, anthracenylene, phenanthrenylene, quinolinylene, dibenzothiophenylene, thioxanthone, thioxanthenylene, or a combination comprising at least one of the foregoing, each $R^2$ and $R^3$ is independently a substituted $C_{5-20}$ aryl not identical to Ar, or a $C_{1-20}$ alkyl, and L is a substituted or unsubstituted $C_{2-20}$ alkylene, and $Z^-$ is a sulfate, sulfonate, or the anion of a sulfonimide.

19. The method of claim 15, wherein the compound has one of formulas (IIIa) to (IIIg):

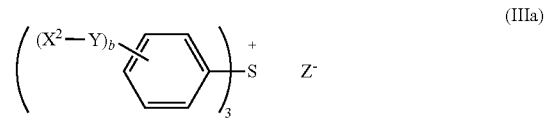

(IIIa)

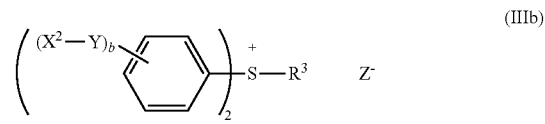

(IIIb)

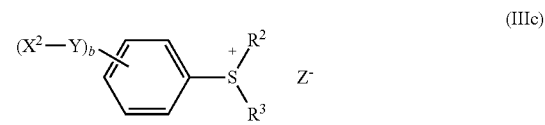

(IIIc)

-continued

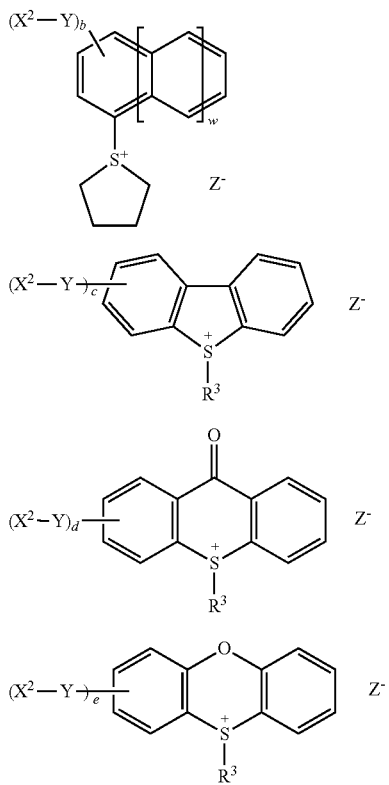

wherein b is an integer of from 1 to 5, w is 0 or 1, and c, d, and e are each an integer of from 1 to 8;

X² is a C₃₋₁₀ organic group containing a 1,1,1,3,3,3-hexafluoroisopropanol-containing group, Y is —O—, —S—, NR—, —O—C(=O)—, —C(=O)—O—, —O—C(=O)—O—, —OCH₂—(C=O)O—, —OCH₂C(=O)—, —SO₂—, —O—SO₂—, or a combination comprising at least one of the foregoing groups, and R is H or C₁₋₆ alkyl, each R² and R³ is independently a substituted C₅₋₂₀ aryl not identical to Ar, or a C₁₋₂₀ alkyl, and L is a substituted or unsubstituted C₂₋₂₀ alkylene, and Z⁻ is a carboxylate, sulfate, sulfonate, sulfamate, or the anion of a sulfonimide.

20. The method of claim 15, wherein Z⁻ has the formula (II):

$$A\text{-}(L)\text{-}(C(R^4)_2)_m\text{-}(C(R^5)_2)_n\text{-}SO_3^- \qquad (II)$$

wherein

A is a substituted or unsubstituted, monocyclic, polycyclic, or fused polycyclic C₃ or greater cycloaliphatic group optionally comprising O, S, N, F, or a combination comprising at least one of the foregoing, or a C₃ or greater aliphatic or cycloaliphatic group containing a polymerizable double or triple bond, R⁴ is H, a single bond, or a substituted or unsubstituted C₁₋₃₀ alkyl group, wherein when R⁴ is a single bond, R⁴ is covalently bonded to a carbon atom of A, each R⁵ is independently H, F, or C₁₋₄ fluoroalkyl, wherein at least one R⁵ is not hydrogen, L is a linking group comprising an —O—, —S—, —C(=O)—, carbonate, carboxylate, sulfonate, sulfate, or a sulfonamide group, and q is an integer of 0 to 10, m is an integer of greater than or equal to 0, and n is an integer of greater than or equal to 1.

* * * * *